US007192417B2

(12) United States Patent  
Thompson et al.

(10) Patent No.: US 7,192,417 B2
(45) Date of Patent: Mar. 20, 2007

(54) INJECTORS AND SYRINGE INTERFACES FOR SYRINGES OF VARIABLE SIZE

(75) Inventors: Jeffrey John Thompson, Allison Park, PA (US); David M. Reilly, Glenshaw, PA (US); Matthew Beale, Pittsburgh, PA (US); Drew Degentesh, Pittsburgh, PA (US); Matthew Goodworth, Pittsburgh, PA (US); Robert Parks, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 572 days.

(21) Appl. No.: 10/233,844

(22) Filed: Sep. 3, 2002

(65) Prior Publication Data

US 2003/0045789 A1 Mar. 6, 2003

Related U.S. Application Data

(60) Provisional application No. 60/317,255, filed on Sep. 5, 2001.

(51) Int. Cl.
*A61M 37/00* (2006.01)

(52) U.S. Cl. .................. 604/154; 604/155; 604/128; 600/432

(58) Field of Classification Search ................ 604/151, 604/131, 134, 154, 155, 181, 187; 600/432
See application file for complete search history.

(56) References Cited

U.S. PATENT DOCUMENTS 5,814,015 A * 9/1998 Gargano et al. ............... 604/67

(Continued)

FOREIGN PATENT DOCUMENTS

EP 1110569 A2 * 6/2001

(Continued)

OTHER PUBLICATIONS

International Search Report for Counterpart PCT Application No. PCT/US02/27878.

*Primary Examiner*—Nicholas Lucchesi
*Assistant Examiner*—Aamer S. Ahmed
(74) *Attorney, Agent, or Firm*—Gregory Bradley; Jill Denesvich

(57) ABSTRACT

A syringe interface for attaching syringes to a drive mechanism which includes a drive member to impart motion to a syringe plunger includes a plurality of syringe mount apertures having different dimensions to attach each of a plurality of syringes to the syringe interface. Each of the syringes for attachment to the syringe interface includes at least one mounting flange, and each of the plurality of syringes has a different mounting flange dimension. Each of the plurality of syringe mount apertures is in general alignment with an axis of the drive member. A syringe drive mechanism includes a syringe interface as described above. The syringe drive mechanism can further include a sensing system to sense which size of the plurality of syringes is mounted on the syringe interface. The syringe drive mechanism can also include a processor and a memory which are in operative communication with the drive member. The memory includes a control program stored therein. The processor is in communication with the sensing system so that the control program controls the drive member according to the syringe sensed to be attached to the syringe interface. A powered injector includes a drive member and a drive to deliver power to the drive member. A processor of the powered injector is in communication with the drive and with a memory in which at least one control program is stored. The control program includes instructions for control of the drive. The powered injector further includes a syringe interface as described above for attaching syringes to the powered injector so that the drive member can impart motion to a plunger slidably positioned within each of the syringes. The powered injector further includes a sensing system to detect which of the syringes is attached to the syringe interface. The sensing system is in communication with the processor so that the control program controls the drive in a manner determined by the syringe detected to be attached to the syringe interface.

26 Claims, 10 Drawing Sheets

U.S. PATENT DOCUMENTS

| | | | |
|---|---|---|---|
| 5,944,694 A * | 8/1999 | Hitchins et al. | 604/154 |
| 6,004,292 A * | 12/1999 | Battiato et al. | 604/123 |
| 6,312,410 B1 | 11/2001 | Yamamoto | |

FOREIGN PATENT DOCUMENTS

| | | |
|---|---|---|
| JP | 09122234 | 5/1997 |
| WO | WO 01/37903 | 5/2001 |
| WO | WO 02/070049 | 9/2002 |

* cited by examiner

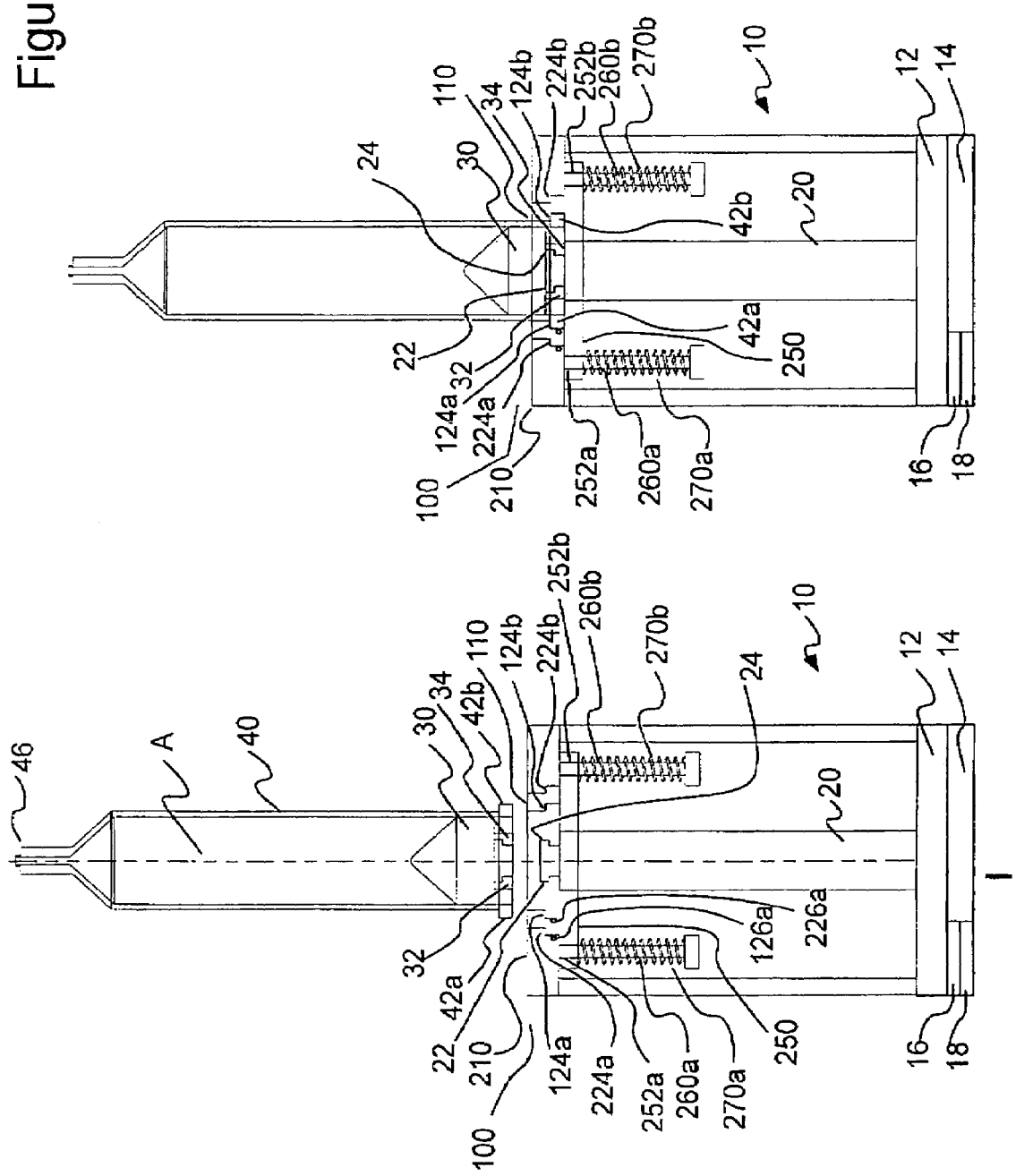

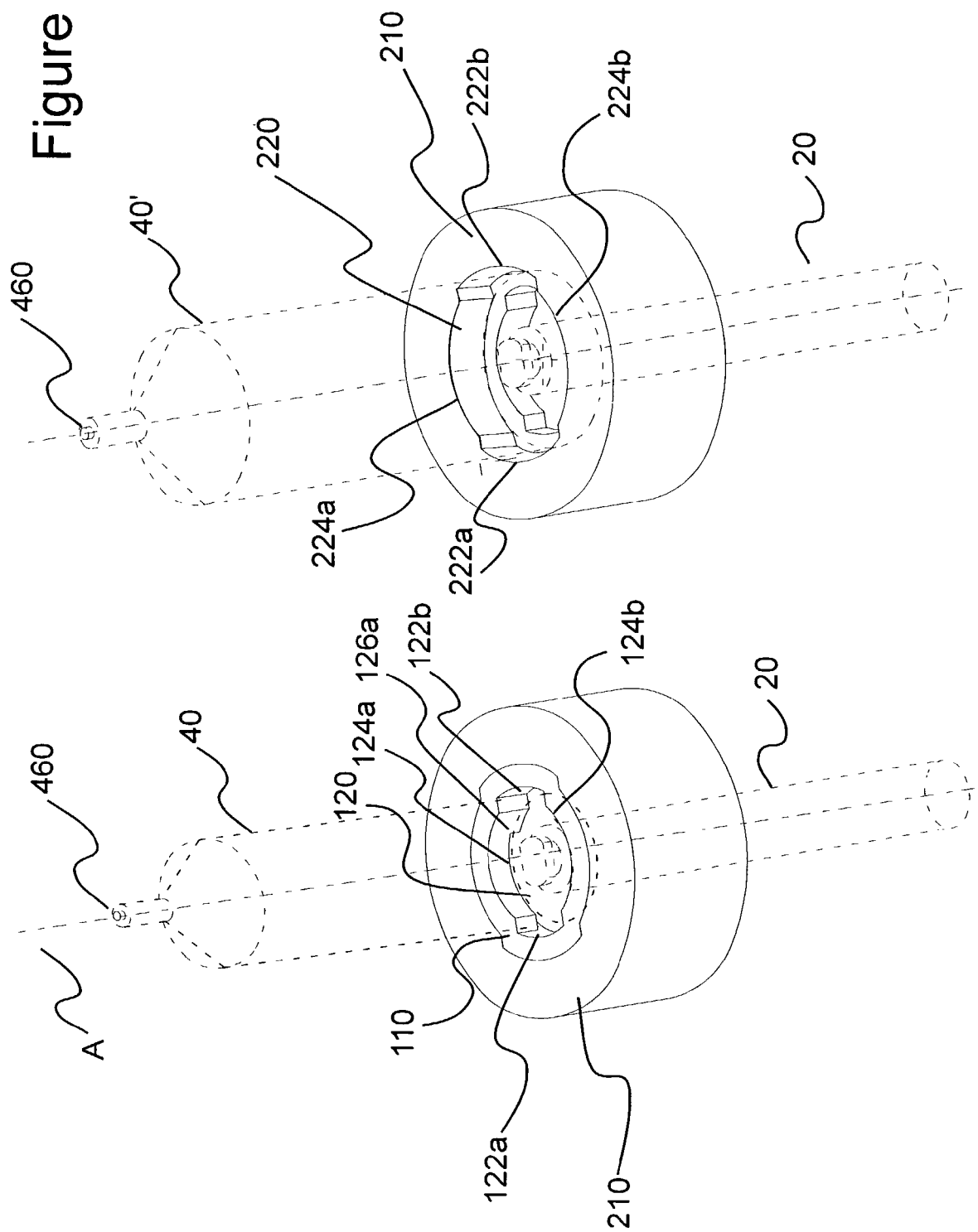

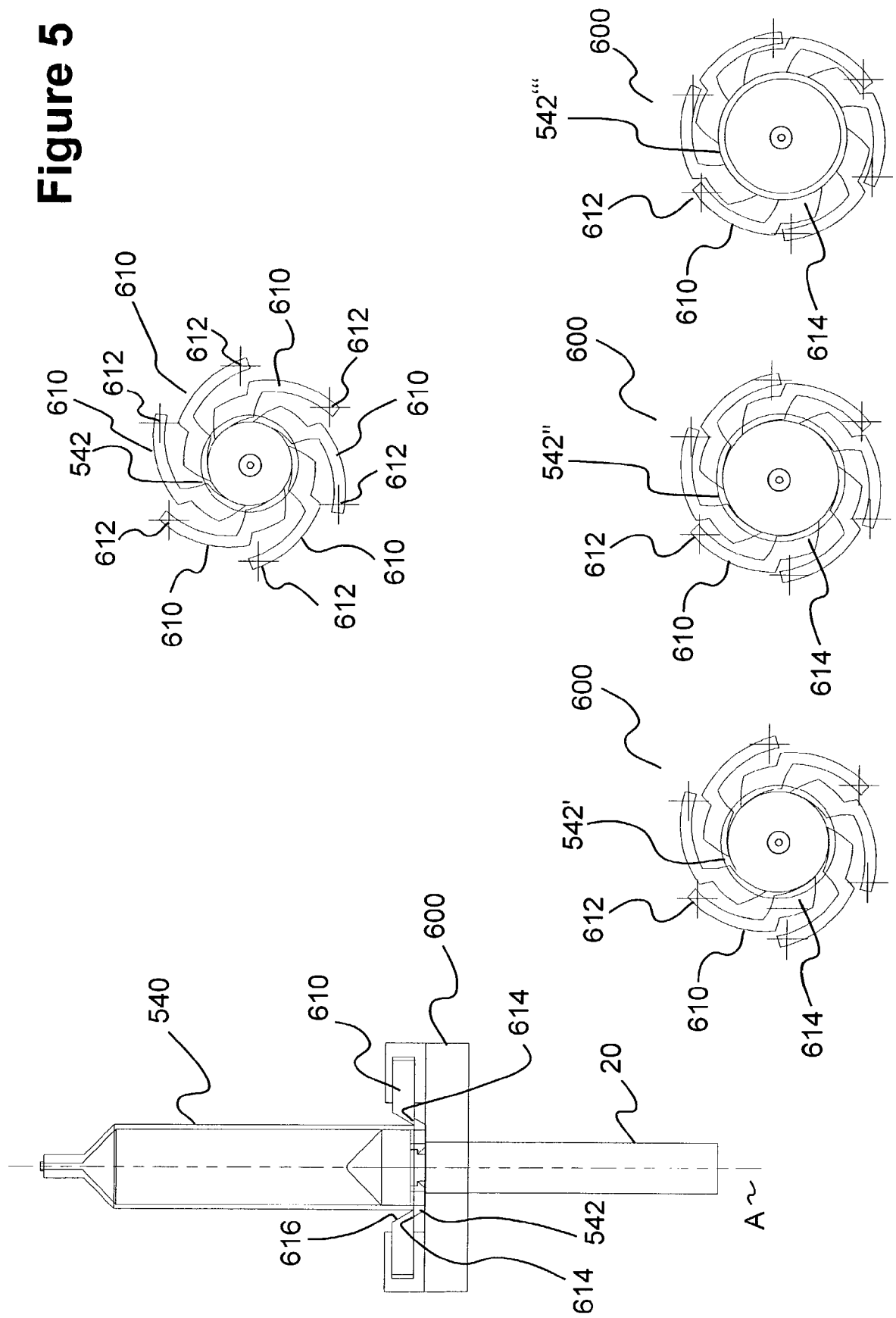

INJECTORS AND SYRINGE INTERFACES FOR SYRINGES OF VARIABLE SIZE

CROSS REFERENCE TO RELATED APPLICATION

This application claims the benefit of U.S. Provisional Application Ser. No. 60/317,255, filed on Sep. 5, 2001, the contents of which are incorporated herein by reference.

BACKGROUND OF THE INVENTION

The present invention relates to syringe interfaces and, particularly, to syringe interfaces for use with syringes of variable size and to syringe drives including such syringe interfaces.

A number of injector-actuated syringes and powered injectors for use in medical procedures such as angiography, computed tomography, ultrasound and magnetic resonance imaging (MRI) have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

The front-loading injector of U.S. Pat. No. 5,383,858 includes a releasable mounting mechanism for securing the syringe to the front wall of the injector. Other types of releasable mounting mechanisms for front-loading syringes are disclosed in PCT International Patent Application PCT/US00/31991, filed Nov. 21, 2000, entitled Front Loading Medical Injector and Syringes, Syringe Interfaces, Syringe Adapters and Syringe Plungers for User Therewith, and U.S. patent application Ser. No. 09/448,484, filed Nov. 24, 1999, entitled Front Loading Medical Injector and Syringes, Syringe Interfaces, Syringe Adapters and Syringe Plungers for User Therewith, assigned to the assignee of the present invention, the disclosures of which are incorporated herein by reference There is a need to use various size (e.g., volume) syringes in connection with powered injectors to best accommodate a procedure being performed on a particular patient. However, the use of specifically designed mounting mechanisms generally prevents the use of syringes of various types and/or sizes with front-loading injectors. Syringe adapters attachable to those front-loading injectors are sometimes used to allow the use of multiple syringes with the front-loading injectors. For example, U.S. Pat. No. 5,520,653 discloses several adapters designed to allow the use of various syringes with a front-loading injector. Other adapters for front-loading injectors are disclosed, for example, in U.S. patent application Ser. No. 09/365,285 filed Jul. 30, 1999 and in U.S. patent application Ser. No. 09/633,299 filed Aug. 8, 2000, assigned to the assignee of the present invention, the disclosures of which are incorporated herein by reference. Although adapters greatly facilitate the attachment of syringes of various types and sizes to a single injector or other syringe drive mechanism, manual installation of such adaptors absorbs valuable operator and injector time. Moreover, storage and tracking of multiple adapters can be a problem. It is also necessary for the operator to make injector program changes to insure that the proper flow characteristics are met for each of different syringe sizes.

An injector can also include a multi-position turret that can be moved from one position to the another position to mount multiple syringes. An injector having a two-position turret is disclosed, for example, in U.S. Pat. No. 4,006,736. In such injectors, the user must physically change the position of the mechanical turret to accommodate different syringes. Moreover, the injector must be programmed by the user for the two different syringes Other injectors use the same interface for syringes of different volume but such syringes must be of the same diameter and of different length. A smaller volume syringe in such a system will have the same inherent accuracy problems as a larger volume syringe. Such a system may not be suitable, for example, for use with pediatric patients where very small volumes are injected.

It is very desirable to develop syringe interfaces that can be used with syringes of various size to facilitate attachment of such syringes to injectors, loaders and other devices in connection with which syringes are used.

SUMMARY OF THE INVENTION

In one aspect, the present invention provides a syringe interface for attaching syringes to a drive mechanism which includes a drive member to impart motion to a syringe plunger. Each of the syringes for attachment to the syringe interface includes at least one mounting mechanism (for example, a mounting flange). The syringe interface includes a plurality of syringe mount apertures preferably having different dimensions to attach each of a plurality of syringes to the syringe interface. In that regard, each of the plurality of syringes preferably has a different mounting flange dimension (as well as a different diameter/volume). Each of the plurality of syringe mount apertures is in general alignment with an axis of the drive member such that the drive member can pass therethrough to impart motion to the syringe plunger.

In one embodiment, each of the syringe mount apertures of the syringe interface includes at least one retaining flange. The retaining flange of each syringe mount aperture preferably projects radially inwardly to a different radial position. Each syringe mount aperture can, for example, include a set of a plurality of retaining flanges. Each set of retaining flanges extends radially inwardly to create a unique aperture dimension. Each syringe mount aperture preferably further includes at least one mounting slot between the retaining flanges to allow passage of each mounting flange on one of the syringes therethrough. In one embodiment, the mounting flanges on the syringe are rotatable relative to the retaining flanges of the syringe mount aperture to be positioned in abutting cooperation with the retaining flanges of the syringe mount aperture.

In one embodiment, each set of retaining flanges includes two retaining flanges positioned generally opposite of each other. Two generally opposing mounting slots are positioned between the retaining flanges of each set of retaining flanges to cooperate with two generally opposing mounting flanges on one of the syringes.

At least one of the sets of retaining flanges can be movable in an axial direction relative to another set of retaining flanges. For example, the syringe interface can include a first inner set of retaining flanges for cooperation with a first syringe and a second outer set of retaining flanges for cooperation with a second syringe, the second syringe having a diameter larger in diameter than the first syringe. The first inner set of retaining flanges can be movable in an axial direction when contacted by the second syringe to allow the second syringe to move rearward to cooperate with the second outer set of retaining flanges. The first inner set of retaining flanges can be biased in an axial forward position.

In another embodiment each set of retaining flanges is fixedly positioned at a different axial position. The radial position of the set of retaining flanges (and thus the mounting aperture size) decreases when moving axially rearward.

In still another embodiment, the syringe interface can include a generally cone-shaped or frustum-shaped threaded flange to cooperate with a corresponding threaded flange on each of the plurality of syringes. The radius of the threaded flange on the syringe interface decreases as one moves rearward within the syringe interface.

In a further embodiment, the syringe interface includes a plurality of retention members, each of which includes a retaining flange on one end thereof. The retention members are movable to adjust the radial position of the retaining flanges to cooperate with and retain each of the plurality of syringes. For example, each retention member can be rotatable in a plane generally parallel to an axis of the syringe. Each retention member can alternatively be rotatable in a plane generally parallel to the radius of the syringe.

In another aspect, the present invention provides a syringe interface for attaching each of a plurality of syringes of different size to a drive mechanism. The syringe interface includes a plurality of syringe mounts positioned on the syringe interface generally about a common point or passage corresponding generally to an axis of the drive member of the drive mechanism. Each of the plurality of syringe mounts cooperates with one of the of the syringes to attach the syringe to the syringe interface.

In a further aspect, the present invention provides a syringe interface for attaching each of a plurality of syringes of different size (for example, diameter/volume) to a syringe drive mechanism including a plurality of movable flange members positioned on the syringe interface. Each of the flange members is movable to different radial positions to cooperate with mounting flanges on each of the syringes.

In further aspect, the present invention provides a syringe drive mechanism including a drive member and a syringe interface for attaching syringes to the syringe drive mechanism. Each of the syringes includes at least one mounting flange. The syringe interface includes a plurality of syringe mount apertures having different dimensions to attach each of a plurality of syringes to the syringe interface. Each of the plurality of syringes has a different mounting flange dimension. Each of the plurality of syringe mount apertures is in general alignment with an axis of the drive member as discussed above.

The syringe drive mechanism can further include a sensing system to sense which size of the plurality of syringes is mounted on the syringe interface. Likewise, the syringe drive mechanism can further include a processor and a memory which are in operative communication with the drive member. The memory includes a control program stored therein. Preferably, the processor is in communication with the sensing system so that the control program controls the drive member according to the syringe sensed to be attached to the syringe interface.

In another aspect, the present invention provided a powered injector including a drive member and a drive to deliver power to the drive member. A processor of the powered injector is in communication with the drive and with a memory in which at least one control program is stored. The control program includes instructions for control of the drive. The powered injector further includes a syringe interface as described above for attaching syringes to the powered injector so that the drive member can impart motion to a plunger slidably positioned within each of the syringes. Each of the syringes includes at least one mounting flange. As discussed above, the syringe interface can include a plurality of syringe mount apertures having different dimensions to attach each of a plurality of syringes to the syringe interface. Each of the plurality of syringes preferably has a different mounting flange dimension. Each of the plurality of syringe mount apertures is preferably in general alignment with an axis of the drive member. The powered injector further includes a sensing system to detect which of the syringes is attached to the syringe interface. The sensing system is in communication with the processor so that the control program controls the drive in a manner determined by the syringe detected to be attached to the syringe interface.

In still a further aspect, the present invention provides a method of operating a powered injector including a syringe interface for removably attaching a plurality of syringes to the injector. The syringe interface includes a common passage through which a drive member of the injector can communicate with a plunger slidably disposed within each of the syringes as generally described above. The method including the steps: attaching a first syringe having a first diameter to the syringe interface using a first mounting aperture on the syringe interface, the first mounting aperture being generally aligned with the common passage; removing the first syringe from the syringe interface; and attaching a second syringe having a second diameter different from the first syringe diameter to the syringe interface using a second mounting aperture of the syringe interface, the second mounting aperture being generally aligned with the common passage. The use of adapters or mechanical alteration of the injector mechanics by the user/operator is not necessary in mounting different syringes to the syringe interface of the injector.

In one embodiment, the syringe interface includes a plurality of syringe mounts positioned on the syringe interface about the common passage, each of the plurality of syringe mounts having a different mounting aperture. In another embodiment, the syringe interface includes a plurality of movable flange members positioned on the syringe interface, the flange members being movable to different radial positions to create different mounting apertures.

The method can also include the step of sensing which syringe is attached to the syringe interface. Likewise, the method can include the steps of communicating information of the configuration (for example, diameter, volume etc.) of the attached syringe sensed to be attached to the syringe interface to a processor of the injector, and controlling the drive member in an injection procedure with the processor in a manner determined by the configuration of the attached syringe.

The present invention thus provides generally syringe interfaces that can accept syringes of various sizes. The syringe interfaces include multiple mount apertures that mount together and stay on the injector or other syringe drive mechanism. As the syringe is positioned upon the syringe interface, the proper mount engages the syringe without the need for the operator to attach an adapter to the drive mechanism or to adjust the drive mechanism. Preferably, the syringe drive mechanism (and particularly powered injectors) can sense which syringe is mounted thereon and can automatically program the syringe drive mechanism to the proper syringe configuration.

The syringe interfaces of the present invention are always ready to accept different size syringes and different syringe configurations. There are no extraneous parts (such as syringe adapters currently used in medical procedures) that can be misplaced or improperly used. No parts (such as turrets) upon the syringe drive mechanism must be changed. Moreover, there are no problems associated with user configuration to match syringe size. Thus, multiple diameter size syringes can be used to their best advantage.

The syringe interfaces of the present invention can also be fabricated from material suitable for use in MR environments. For example, polymeric materials and nonferrous metallic materials can be used therein. Polymeric materials that are lubricious, low friction and/or "non-stick" can, for example, be used. Examples of suitable polymeric materials include polycarbonate and DELRIN® available from E.I. duPont de Nemours & Co. of Wilmington, Del.

BRIEF DESCRIPTION OF THE DRAWINGS

Other aspects of the invention and their advantages will be discerned from the following detailed description when read in connection with the accompanying drawings, in which:

FIG. 1A illustrates a side, cross-sectional view of one embodiment a syringe interface of the present invention with a smaller of two syringes positioned for attachment to the syringe interface and also attached to the syringe interface.

FIG. 1D illustrates a perspective view of the syringe interface portions of FIG. 1C with two different sized syringes (illustrated in dashed lines) connected thereto.

FIG. 5 illustrates a side, cross-sectional view a further embodiment of a syringe interface of the present invention including a plurality of adjustable/rotatable flange arms to attach syringes of various size thereto.

DETAILED DESCRIPTION OF THE INVENTION

Figure 1B:
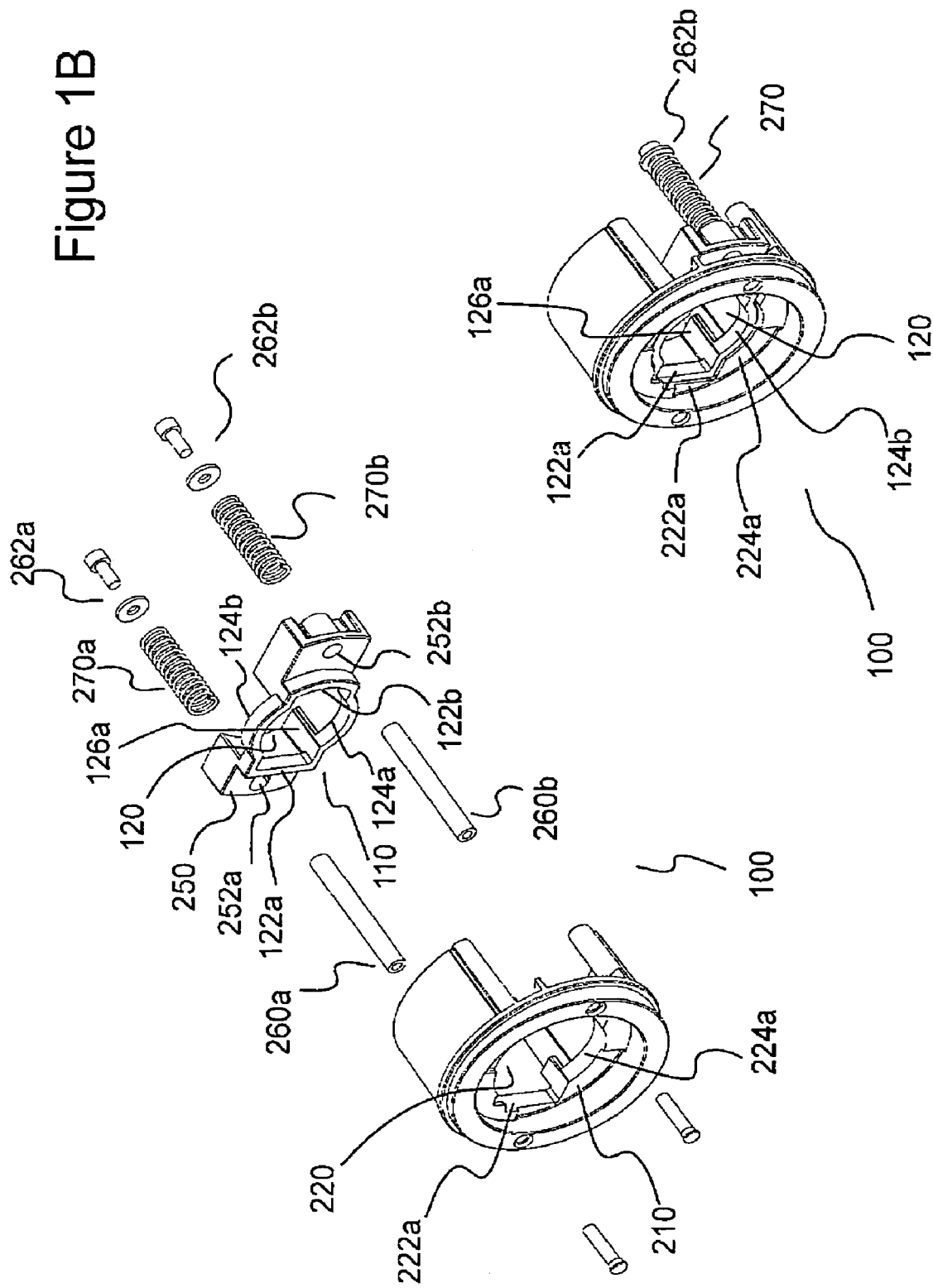
FIG. 1B illustrates a disassembled or exploded perspective view of the syringe interface of FIG. 1A and an assembled perspective view of the syringe interface.
Figure 1C:
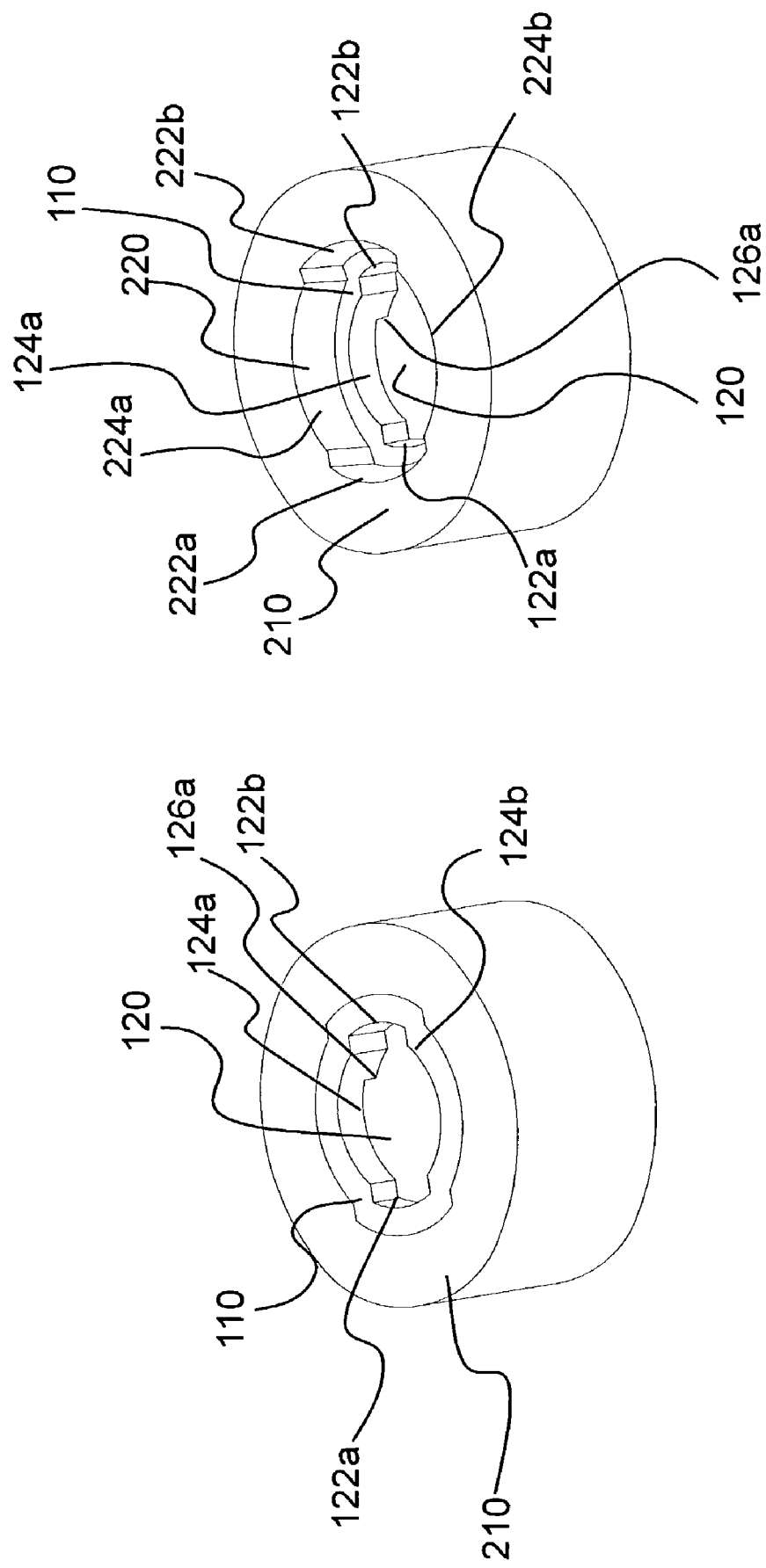
FIG. 1C illustrates a perspective view of a portion of the syringe interface of FIG. 1A with the first mount in a forward position and also in a rearward position.

The syringe interfaces of the present invention can be used in connection with any device (syringe drive mechanism) to which a syringe is typically connected. For example, the syringe interfaces of the present invention can be incorporated into powered injectors as described above, into manual injectors or into syringe loaders as, for example, described in U.S. Provisional Patent Application Ser. No. 60/267,303, filed Feb. 8, 2001 and entitled SYRINGE LOADERS FOR USE WITH MEDICAL INJECTORS, assigned to the assignee of the present invention, the disclosure of which is incorporated herein by reference.

An embodiment of a front-loading injector (or other syringe drive mechanism) 10 including one embodiment of a syringe interface of the present invention is illustrated in FIGS. 1A through 1E. Injector or other syringe drive mechanisms 10 includes a drive member 20 which imparts motion to a plunger 30 slideably positioned within a syringe 40 as known in the art. Plunger 30 is preferably removably connectable to drive member 20 via, for example, capture members 32 and 34 which cooperate with flanges 22 and 24 of drive member 20 as further described, for example, in U.S. Pat. No. 5,383,858, the disclosure of which is incorporated herein by reference. Drive member 20 can be powered or operated manually. In the case of a powered injector, injector 10 includes a powered drive mechanism 12 shown schematically in FIG. 1A (for example, a drive screw powered by an electric motor) as known in the art. Syringe 40 includes flanges 42a and 42b which cooperate with a syringe interface 100 as described below to removably attach syringe 40 to injector 10.

As used herein, the terms "axial" or "axially" refer generally to, for example, an axis A around which syringe 40 and drive member 20 are preferably formed (although not necessarily symmetrically therearound) and to directions collinear with or parallel to such an axis. The terms "proximal" or "rearward" refer generally to an axial or a longitudinal direction toward the end of syringe 40 opposite a syringe tip 46 (from which pressurized fluid exits syringe 40). The terms "distal" or "forward" refer generally to an axial or a longitudinal direction toward the syringe tip 46 of syringe 40. The term "radial" refers generally to a direction normal to an axis such as axis A.

Syringe 40 can, for example, be removably connected to injector 10 generally as described in U.S. Pat. No. 5,383,858, the disclosure of which is incorporated herein by reference. In that regard, syringe interface 100 can include a first mount or mount aperture 110 having a first opening 120 formed therein. Drive member 20 is reciprocally mounted within injector 10 and is extendible through opening 120. Mount 110 includes receiving slots 122a and 122b, which are preferably positioned opposite one another around opening 120. Receiving flanges 124a and 124b are preferably positioned opposite one another, between receiving slots 122a and 122b, and extend inwardly into opening 120.

To attach syringe 40 to injector 10, the rearward end of syringe 40 is inserted into injector opening 120 such that mounting flanges 42a and 42b are inserted into receiving slots 122a and 122b, respectively. In one embodiment, piston flanges 22 and 24 are preferably simultaneously aligned to engage capture members 32 and 34 on the rear of syringe plunger 30 (as, for example, described in U.S. Pat. No. 5,383,858) when mounting flanges 42a and 42b are aligned with slots 122a and 122b. As clear to one skilled in the art, however, many other plunger and piston designs are possible to connect the piston to the plunger.

Once mounting flanges 42a and 42b are inserted into receiving slots 122a and 122b, respectively, and piston 20 is in position to be received by plunger 30, the operator rotates syringe 40 approximately 90 degrees such that mounting flanges 42a and 42b move behind and are engaged by receiving flanges 124a and 124b, respectively, and piston flanges 22 and 24 are retained by, for example, L-shaped capture members 32 and 34. Syringe interface 100 may include one or more stop mechanisms such as, for example, abutment member 126a extending, for example, from at least one of the retaining flanges 124a and 124b, to prevent rotation of syringe 40 more than 90 degrees. Tactile, visual or audible feedback can be provided to the operator via, for example, cooperating members (not shown) on syringe 40 and syringe interface 100 to inform the operator that secure connection has been achieved. After securely attaching syringe 40 to syringe interface 100 (and thereby to injector 10), advancing drive member 20 in a forward direction will apply a motive force to plunger 30 to advance plunger 30 forward within syringe 40, thereby forcing the contents of syringe 40 out of syringe tip 46. Retracting drive member 20 in a rearward direction will cause plunger 30 to move rearward within syringe 40, thereby drawing fluid into syringe 40.

Syringe interface 100 also includes at least a second mount or mount aperture 210 having an opening 220 formed therein that is larger than opening 120 and has generally the same center as opening 120 corresponding generally to axis A of drive member 20. Drive member 20 is thus also extendible through opening 220 to cooperate with plunger 30 as described above. Mount 210 includes receiving slots 222a and 222b, which are preferably positioned opposite one another around opening 220. Retaining flanges 224a and 224b are preferably positioned opposite one another between receiving slots 222a and 222b and extend inwardly into opening 220.

Figure 1E:
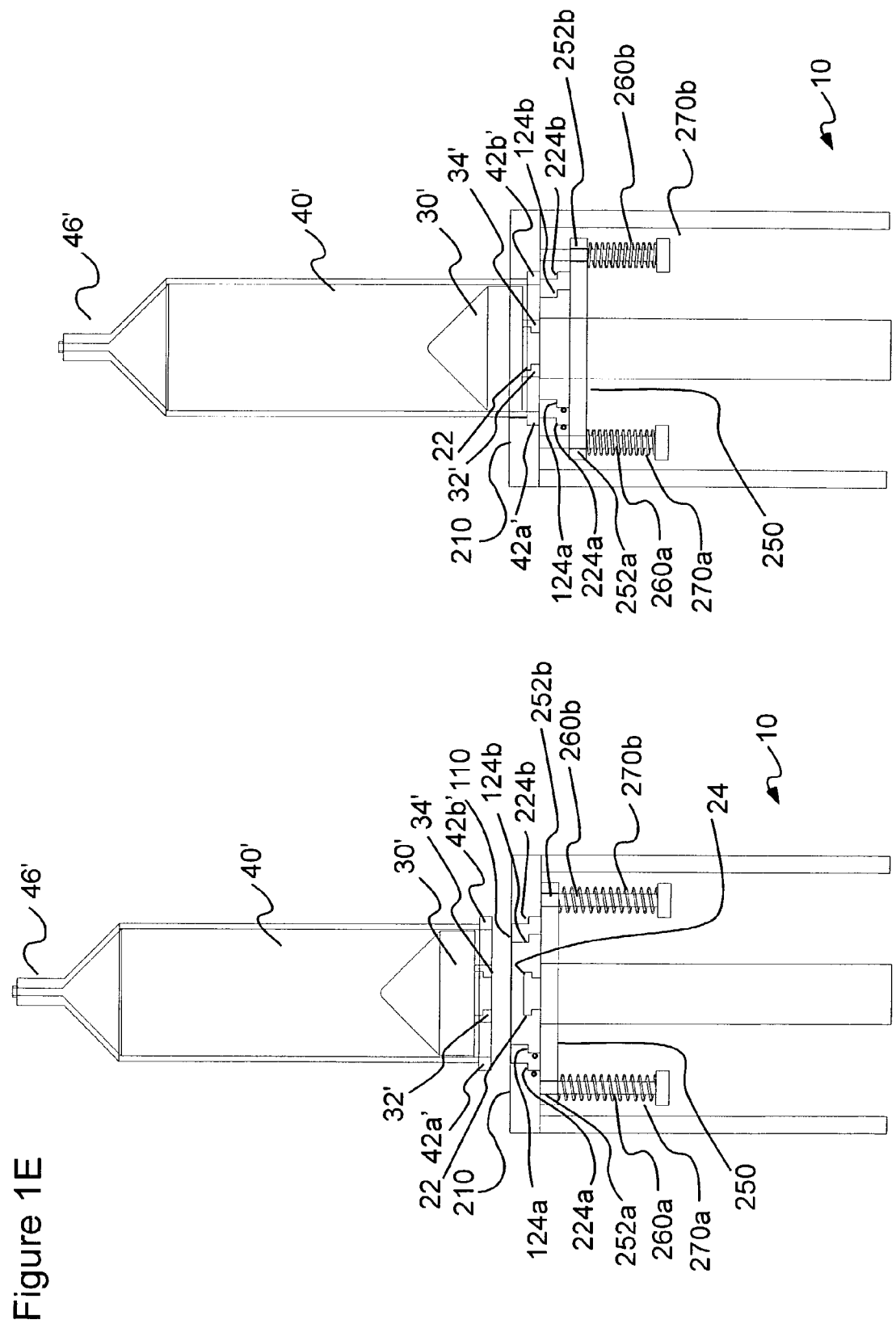
FIG. 1E illustrates a side, cross-sectional view of one embodiment a syringe interface of the present invention with a larger of two syringes positioned for attachment to the syringe interface and also attached to the syringe interface.

To attach a syringe 40' to injector 10, the rearward end of syringe 40' is inserted into injector opening 220 such that mounting flanges 42a' and 42b' are inserted into receiving slots 222a and 222b, respectively (see, for example, FIG. 1E). The diameter of syringe 40' is greater than the diameter of syringe 40. As syringe 40' is moved rearward, it contacts mount 110. Mount 110 is preferably movable (for example, slidable in an axial direction) such that mount 110 moves rearward when contacted by syringe 40'. Axial rearward movement of mount 110, allows syringe 40' to move rearward and, subsequently, to be rotated relative to mount 210 so that flanges 42a' and 42b' of syringe 40' are rotated into general alignment with (that is, behind or to the rear of) retaining flanges 224a and 224b as described above for syringe 40 and retaining flanges 124a and 124b.

In one embodiment, mount 110 is attached to or formed integrally with a plate 250 that is slidably mounted on posts 260a and 260b via holes or passages 252a and 252b, respectively, formed in plate 250. Preferably, mount 110 is biased in a forward position as illustrated, for example, in FIG. 1A. In the embodiment of FIGS. 1A through 1E, springs 270a and 270b are positioned on posts 260a and 260b to bias mount 110 in a forward position. Springs 270a and 270b are retained on posts 260a and 260b by plate 250 and abutment elements 262a and 262b positioned on a rearward end of posts 260a and 260b, respectively.

In the case of, for example, a powered injector, motion of drive member 20 and thus syringe plunger 30 are typically controlled by a control system 14, which can include a processor 16 and a memory 18, in communication with powered drive mechanism 12 (see FIG. 1A). In one embodiment, processor 16 is in communication with a sensing system including, for example, sensors 126a and 226a (see FIG. 1A) positioned on mount 110 and mount 210, respectively. Using sensors 126a and 226a, injector 10 can identify which syringe is mounted on syringe interface 100 and make any adjustments necessary to or with injector control program(s) stored in memory 18 for proper control given the current syringe configuration in a manner known to those skilled in the art. For example, the control program(s) use information on syringe configuration to control the speed at which and the distance to which drive member 20 is advanced for that particular syringe configuration and for a particular patient. Sensors 126a and 226a can be of any type known in the art including, but not limited to, electromechanical switches or optical sensors.

Figure 2A:
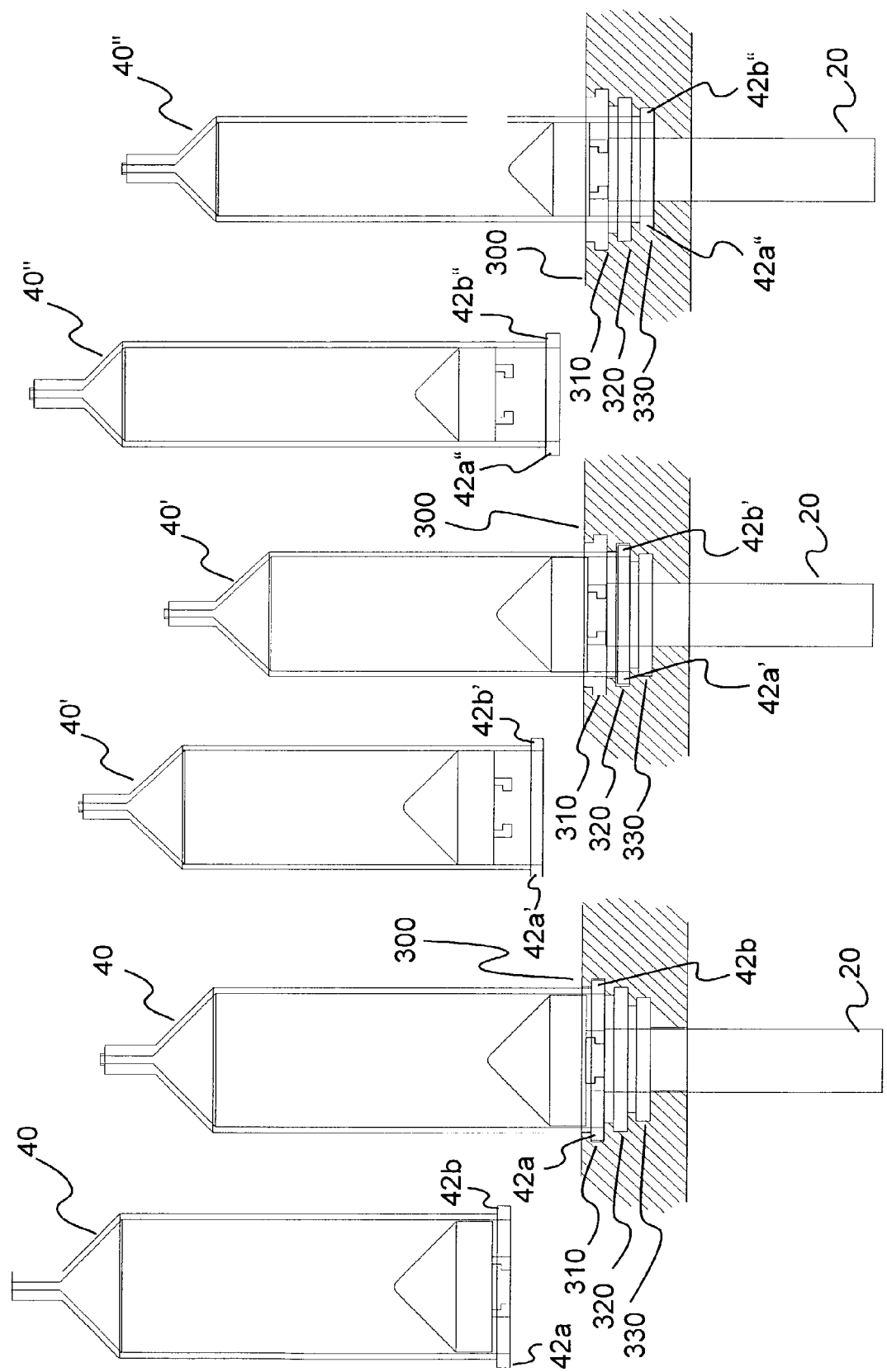
FIG. 2A illustrates a side, cross-sectional view of another embodiment of a syringe interface of the present invention including multiple fixed syringe mounts for mounting syringes of various sizes.
Figure 2B:
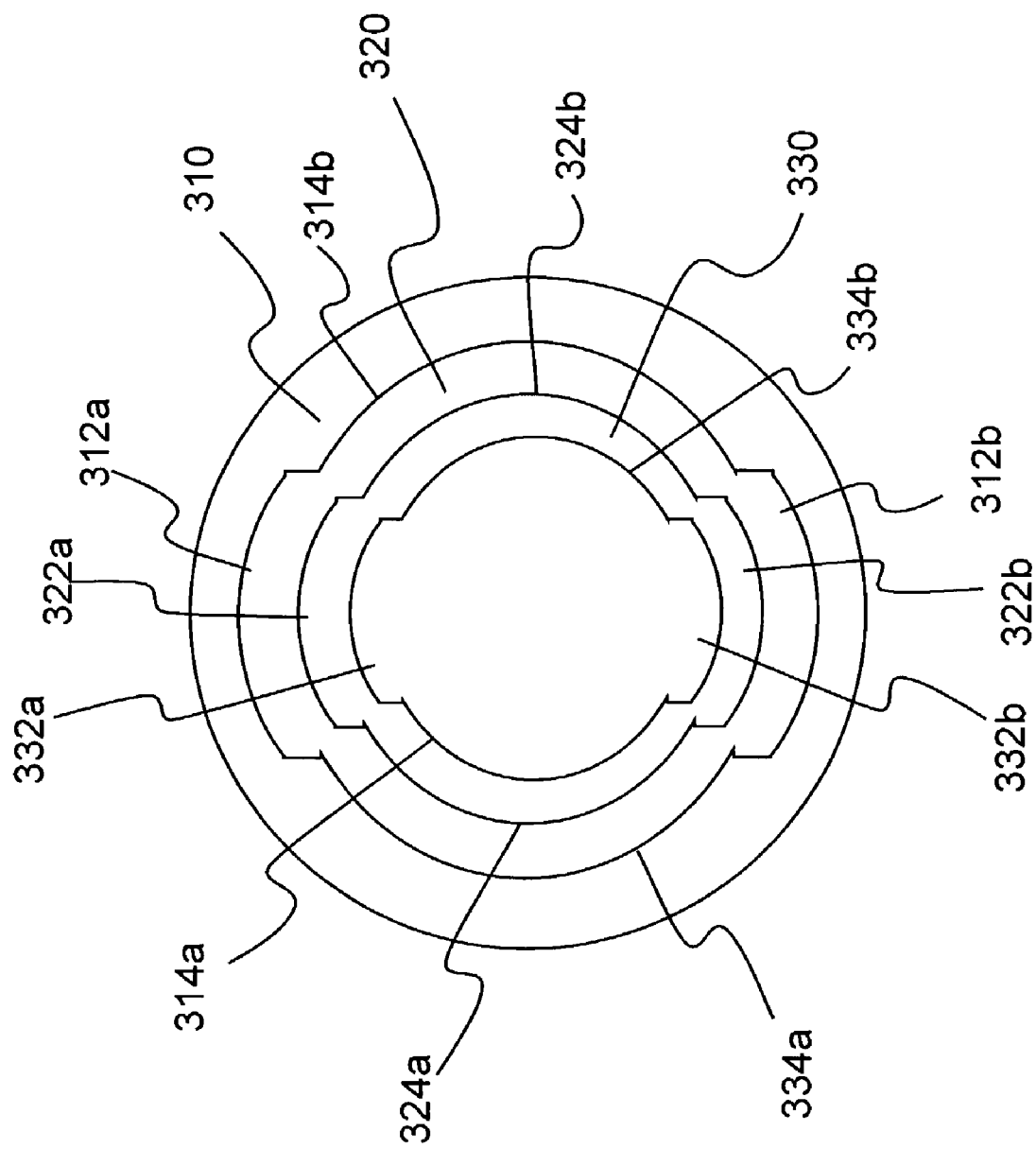
FIG. 2B illustrates a front view of the syringe interface of FIG. 2A.

FIGS. 2A and 2B illustrate another embodiment of a syringe interface 300 of the present invention. In the embodiment of FIGS. 2A and 2B, syringe interface 300 includes a plurality of fixed mounts 310, 320 and 330. Each of mounts 310, 320 and 330 is dimensioned to attach one of different sized syringes 40, 40' or 40", respectively, thereto. As described above, each of syringes 40, 40' and 40" include two generally opposing mounting flanges 42a and 42b, 42a' and 42b', and 42a" and 42b", respectively. Mount 310 thus includes generally opposing mounting slots 312a and 312b and generally opposing retaining flanges 314a and 314b (see FIG. 2B) which operate as described above to removably attach or mount syringe 40 to mount 310. Likewise, mount 320 includes generally opposing mounting slots 322a and 322b and generally opposing retaining flanges 324a and 324b which operate as described above to removably attach or mount syringe 40' to mount 320. Mount 330 includes generally opposing mounting slots 332a and 332b and generally opposing retaining flanges 334a and 334b which operate as described above to removably attach or mount syringe 40" to mount 330.

The passages or apertures of each of mounts 310, 320 and 330 are in general alignment with drive member 20 to allow operative connection between drive member 20 and the syringe plunger. The radius or size of the passage between the retaining flanges of mounts 310, 320 and 330 preferably decreases as one moves axially rearward within syringe interface 300 to enable each of syringes 40, 40' and 40" to move rearward for attachment to corresponding mount 310, 320 or 330, respectively. In other words, mount 310 is dimensioned to attach largest syringe 40 thereto. Mount 320 is dimensioned to attach intermediate size syringe 40' thereto. Mount 330 is dimensioned to attach smallest size syringe 40" thereto. One or more sensor can be provided to indicate which size syringe is attached to syringe interface 300.

Figure 3:
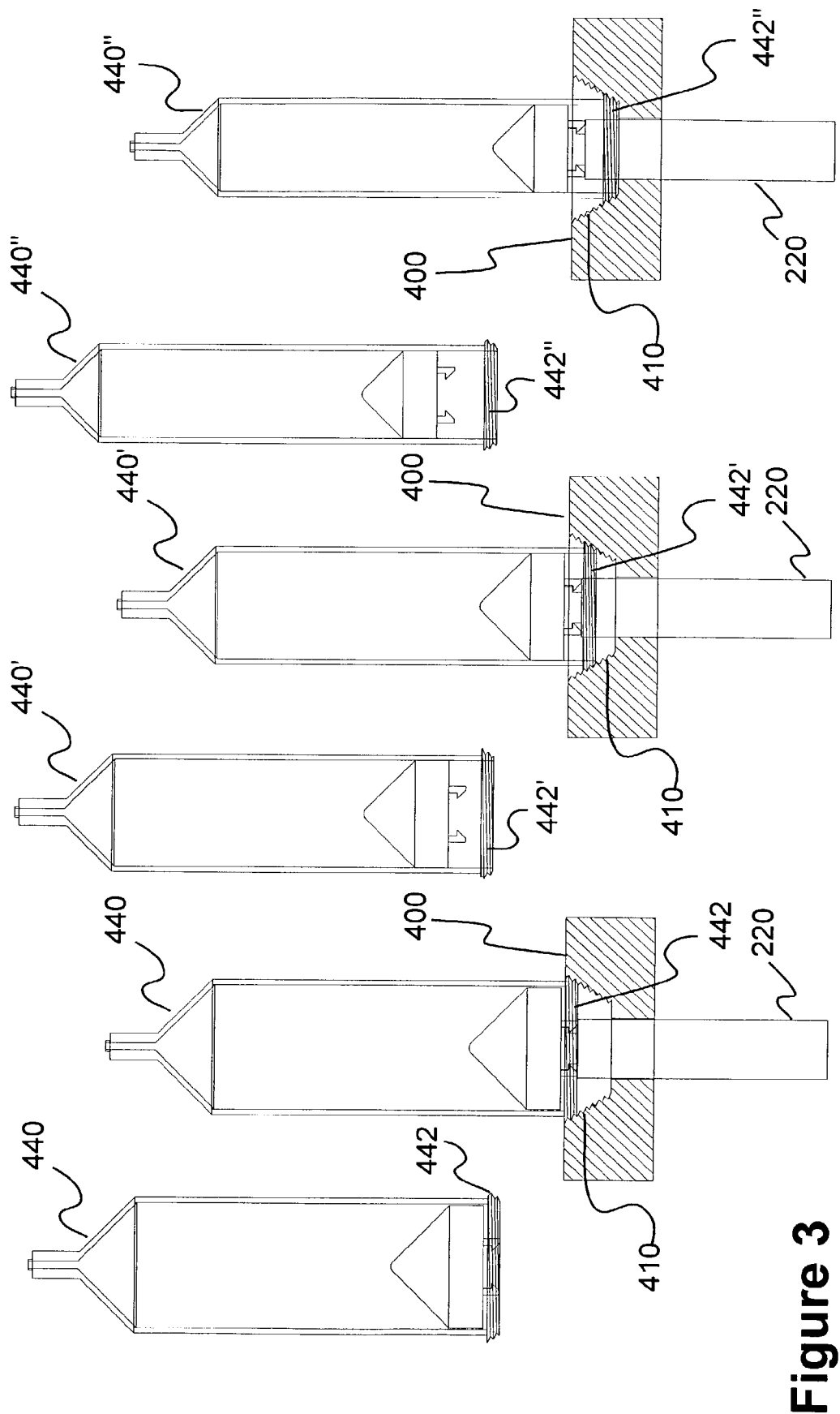
FIG. 3 illustrates a side, cross-sectional view another embodiment of a syringe interface of the present invention including a cone shaped threading for attachment of syringes of various size thereto.

FIG. 3 illustrates another embodiment of the present invention in which a syringe interface 400 includes a tapered or cone-shaped threading 410. The radius of threading 410 decreases as one moves axially rearward within syringe interface 400. Different sized syringes 440, 440' and 440" include corresponding tapered or cone-shaped threaded flanges 442, 442' and 442", respectively. Tapered threaded flanges 442, 442' and 442" cooperate with or thread onto threading 410 of syringe interface 440 as illustrated in FIG. 3 to removably attach syringes 440, 440' and 440" to syringe interface 400. As described above, one or more sensor can be provided to indicate which size syringe is attached to syringe interface 400 (for example, by sensing the axial position of the attached syringe).

Figure 4:
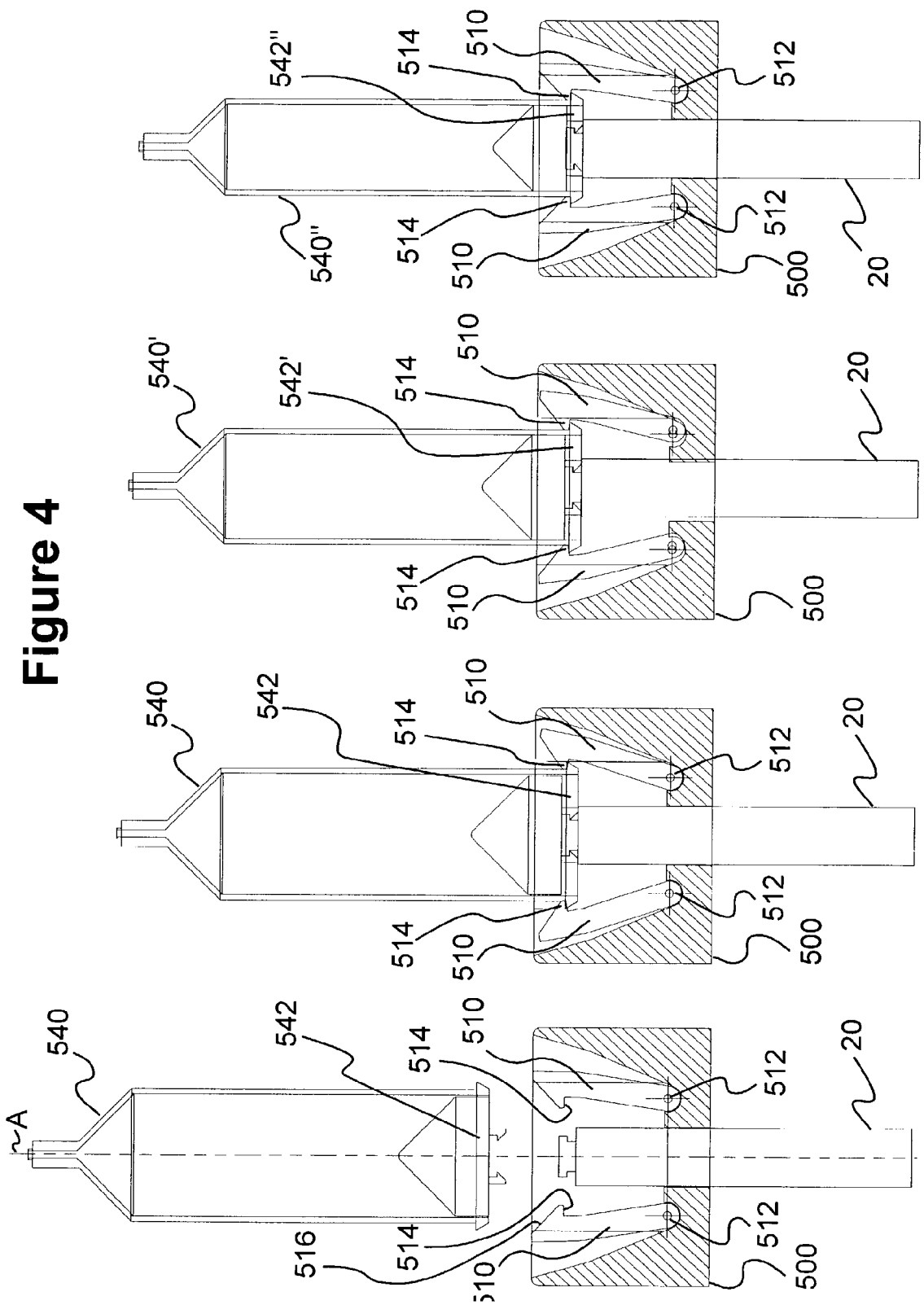
FIG. 4 illustrates a side, cross-sectional view another embodiment of a syringe interface of the present invention including a plurality of adjustable/rotatable flange arms to attach syringes of various size thereto.

FIGS. 4 and 5 illustrate embodiments of the present invention including a mount mechanism of variable size to removably attach syringes of various size thereto. In the embodiment of FIG. 4, syringe interface 500 includes a plurality of flange arms 510 that rotate (in a plane generally parallel to axis A of, for example, syringe 540) about, for example, a pin 512 on a rearward end thereof, so that the radial position of a radially inward projecting flange 514 on a forward end thereof can be varied. Rotating flange arms 510 about pins 512 thus changes the effective radius of a composite retaining flange formed by the plurality of inward projecting flanges 514 to accommodate syringes of various size.

Syringes 540, 540' and 540" can, for example, include a generally circumferential flange 542, 542' and 542", respectively. Syringes having multiple, partially circumferential flanges such as syringes 40, 40' and 40" can also be used with syringe interface 500. As illustrates in FIG. 4, flanges 514 cooperate with syringe flange 542, 542' or 542' to removably attach syringes 540, 540' and 540", respectively, to syringe interface 500. Flange arms 510 can be biased about pins 512 (using, for example, springs as known in the art) so that flanges 514 are biased in a radially inward position as illustrated in the far left of FIG. 4. A forward surface 516 of flange arms 514 can be tapered radially inward in an axial direction from forward to rearward such that when one of syringe mounting flanges 542, 542' and 542' contact forward surface 516, rearward movement of syringe 540, 540' and 540" to cooperate with flanges 514 is facilitated. The outer circumference of mounting flanges 542, 542' and 542' can also be tapered in a generally corresponding manner (as illustrated in FIG. 4) to further facilitate engagement.

FIG. 5 illustrates a syringe interface 600 including a plurality of flange arms 610 that rotate about points 612 (for example, pins) on a radial outward end thereof in a plane generally perpendicular to axis A of, for example, syringe 540. Each of flange arms 610 includes a radially inward projecting flange 614 on a radial inward end of flange arm 610 that cooperates with flanges 542, 542', 542" and 542'" to removably attach syringes 540, 540', 540" and 540'" to syringe interface 600. In that regard, rotating flange arms 610 about points 612 alters the radial position of inward projecting flanges 514 similar to the manner of an iris. Rotating flange arms 610 about pins 612 thus changes the effective radius of a composite retaining flange formed by the plurality of inward projecting flanges 614 to accommodate syringes of various size and having varying flange diameters. Flange arms 610 can be biased about pins 612 (using, for example, springs as known in the art) so that flanges 614 are biased in a radially inward position as illustrated in the far left of FIG. 5. A forward or front surface 616 of flange arms 614 can be tapered radially inward in an axial direction from forward to rearward such that when one of syringe mounting flanges 542, 542', 542" or 542'" contact front surface 616, rearward movement of syringe 540, 540', 540" or 540'" is facilitated. Like syringe interface 500, syringe interface 600 can be used with circumferential flanges or with partially circumferential flanges.

As with all other embodiments of syringe interfaces of the present invention, syringe interfaces 500 and 600 can include one or more sensors can to detect/indicate which size syringe is attached thereto. For example, the amount of rotation of flange arms 510 or 610 can be detected to determine syringe size. Likewise, the radial position of flange arms 510 or 610 can be directly measured to determine syringe size.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A syringe interface for attaching a plurality syringes having different barrel diameters to a drive mechanism including a drive member, each of the syringes including at least one mounting flange, the at least one mounting flange of syringes of different barrel diameters extending radially outward to different extents, the syringe interface including a plurality of syringe mount apertures having different dimensions to attach each of the plurality of syringes to the syringe interface, each syringe mount aperture being positioned at a different axial position on the syringe interface such that the syringe mount apertures having a larger diameter are positioned forward of the syringe mount apertures having a smaller diameter each of the plurality of syringe mount apertures having an axis in general alignment with an axis of the drive member, each of the syringe mount apertures of the syringe interface comprising at least one retaining flange, the retaining flange of each syringe mount aperture projecting radially inward to a different radial position to cooperate with the at least one mounting flange of one of the syringes, each of the retaining flanges of each of the syringe mount apertures being in general alignment about the circumference of the syringe.

2. The syringe interface of claim 1 wherein each syringe mount aperture includes a set of a plurality of retaining flanges, each set of retaining flanges extending radially inwardly to create a unique aperture dimension, each set of the retaining flanges of each of the syringe mount apertures being in general alignment about the circumference of the syringe, each syringe mount aperture further including at least one mounting slot between the retaining flanges to allow passage of each mounting flange on one of the syringes therethrough, each of the mounting slots of each of the syringe mount apertures being in general alignment about the circumference of the syringe, the mounting flanges on the syringe being rotatable relative to the retaining flanges of the syringe mount aperture to be positioned in abutting cooperation with the retaining flanges of the syringe mount aperture.

3. The syringe interface of claim 2 wherein each set of retaining flanges includes two retaining flanges positioned generally opposite of each other, two generally opposing mounting slats being positioned between the retaining flanges of each set of retaining flanges to cooperate with two generally opposing mounting flanges on one of the syringes.

4. The syringe interface of claim 3 wherein at least one of set of retaining flanges is movable in an axial direction relative to another set of retaining flanges.

5. The syringe interface of claim 4 including a first inner set of retaining flanges for cooperation with a first syringe and a second outer set of retaining flanges for cooperation with a second syringe, the second syringe having a diameter larger than the first syringe, the first inner set of retaining flanges being movable in an axial direction when contacted by the second syringe to allow the second syringe to move rearward to cooperate with the second outer set of retaining flanges.

6. The syringe interface of claim 5 wherein the first inner set of retaining flanges is biased in an axial forward position.

7. The syringe interface of claim 2 wherein each set of retaining flanges is positioned at a different axial position, the aperture dimension created by each of the sets of retaining flanges decreasing when moving axially rearward.

8. The syringe interface of claim 1 including a generally cone-shaped threaded flange to cooperate with a corresponding threaded flange on each of the plurality of syringes.

9. A syringe drive mechanism including a drive member and a syringe interface for attaching a plurality of syringes having different barrel diameters to the syringe drive mechanism, each of the syringes including at least one mounting flange, the at least one mounting flange of syringes of different barrel diameters extending radially outward to different extents, the syringe interface including a plurality of syringe mount apertures having different dimensions to attach each of the plurality of syringes to the syringe interface, each syringe mount aperture being positioned at a different axial position on the syringe interface such that the syringe mount apertures having a larger diameter are positioned forward of the syringe mount apertures having a smaller diameter each of the plurality of syringe mount apertures having an axis in general alignment with an axis of the chive member, each of the syringe mount apertures of the syringe interface comprising at least one retaining flange, the retaining flange of each syringe mount aperture projecting radially inward to a different radial position to cooperate with the at least one mounting flange of one of the syringes, each of the retaining flanges of each of the syringe mount apertures being in general alignment about the circumference of the syringe.

10. The syringe drive mechanism of claim 9 wherein each syringe mount aperture includes a set of a plurality of retaining flanges, each set of retaining flanges extending radially inwardly to create a unique aperture dimension, each set of the retaining flanges of each of the syringe mount apertures being in general alignment about the circumference of the syringe, each syringe mount aperture further including at least one mounting slot between the retaining flanges to allow passage of each mounting flange on one of the syringes therethrough, each of the mounting slots of each of the syringe mount apertures being in general alignment about the circumference of the syringe, the mounting flanges on the syringe being rotatable relative to the retaining flanges of the syringe mount aperture to be positioned in abutting cooperation with the retaining flanges of the syringe mount aperture.

11. The syringe drive mechanism of claim 10 wherein each set of retaining flanges includes two retaining flanges positioned generally opposite of each other, two generally opposing mounting slots being positioned between the retaining flanges of each set of retaining flanges to cooperate with two generally opposing mounting flanges on one of the syringes.

12. The syringe drive mechanism of claim 11 wherein at least one of set of retaining flanges is movable in an axial direction relative to another set of retaining flanges.

13. The syringe drive mechanism of claim 12 including a first inner set of retaining flanges for cooperation with a first syringe and a second outer set of retaining flanges for cooperation with a second syringe, the second syringe having a diameter larger than the first syringe, the first inner set of retaining flanges being movable in an axial direction when contacted by the second syringe to allow the second syringe to move rearward to cooperate with the second outer set of retaining flanges.

14. The syringe drive mechanism of claim 13 wherein the first inner set of retaining flanges is biased in an axial forward position.

15. The syringe drive mechanism of claim 10 wherein each set of retaining flanges is positioned at a different axial position, the aperture dimension created by each of the sets of retaining flanges decreasing when moving axially rearward.

16. The syringe drive mechanism of claim 9 including a generally cone-shaped threaded flange to cooperate with a corresponding threaded flange on each of the plurality of syringes.

17. The syringe drive mechanism of claim 9 further including a sensing system to sense which size of the plurality of syringes is mounted on the syringe interface.

18. The syringe drive mechanism of claim 17 further including a processor and a memory in operative communication with the drive member, the memory ineluding a control program stored therein, the processor being in communication with the sensing system so that the control program controls the drive member according to the syringe sensed to be attached to the syringe interface.

19. A powered injector including a drive member, a drive to deliver power to the drive member, a processor in communication with the drive, the processor also being in communication with a memory in which at least one control program is stored, the control program including instructions for control of the drive, the powered injector further including a syringe interface for attaching a plurality of syringes having different barrel diameters to the powered injector so that the drive member can impart motion to a plunger slidably positioned within eaAzh of the syringes, each of the syringes including at least one mounting flange, the mounting flanges of syringes of different barrel diameters extending radially outwardly to different extents, the syringe interface including a plurality of syringe mount apertures having different dimensions to attach each of the plurality of syringes to the syringe interface, each syringe mount aperture being positioned at a different axial position on the syringe interface such that the syringe mount apertures having a larger diameter are positioned forward of the syringe mount apertures having a smaller diameter each of the plurality of syringe mount apertures having an axis in general alignment with an axis of the drive member, each of the syringe mount apertures of the syringe interface comprising at least one retaining flange, the retaining flange of each syringe mount aperture projecting radially inward to a different radial position to cooperate with one of the mounting flanges of one of the syringes, each of the retaining flanges of each of the syringe mount apertures being in general alignment about the circumference of the syringe, the powered injector further including a sensing system to detect which of the syringes is attached to the syringe interface, the sensing system being in communication with the processor so that the control program controls the drive in a manner determined by the syringe detected to be attached to the syringe interface.

20. The powered injector of claim 19 wherein each syringe mount aperture includes a set of a plurality of retaining flanges, each set of retaining flanges extending radially, inwardly to create a unique aperture dimension, each set of retaining flanges of each of the syringe mount apertures being in general alignment about the circumference of the syringe, each syringe mount aperture further including at least one mounting slot between the retaining flanges to allow passage of each mounting flange on one of the syringes therethrough, each of the mounting slots of each of the syringe mount apertures being in general alignment about the circumference of the syringe, the mounting flanges on the syringe being rotatable relative to the retaining flanges of the syringe mount aperture to be positioned in abutting cooperation with the retaining flanges of the syringe mount aperture.

21. The powered injector of claim 20 wherein each set of retaining flanges includes two retaining flanges positioned generally opposite of each other, two generally opposing mounting slots being positioned between the retaining flanges of each set of retaining flanges to cooperate with two generally opposing mounting flanges on one of the syringes.

22. The powered injector of claim 21 wherein at least one of set of retaining flanges is movable in an axial direction relative to another set of retaining flanges.

23. The powered injector of claim 22 including a first inner set of retaining flanges for cooperation with a first syringe and a second outer set of retaining flanges for cooperation with a second syringe, the second syringe having a diameter larger than the first syringe, the first inner set of retaining flanges being movable in an axial direction when contacted by the second syringe to allow the second syringe to move rearward to cooperate with the second outer set of retaining flanges.

24. The powered injector of claim 23 wherein the first inner set of retaining flanges is biased in an axial forward position.

25. The powered injector of claim 20 wherein each set of retaining flanges is positioned at a different axial position, the aperture dimension created by each of the sets of retaining flanges decreasing when moving axially rearward.

26. The powered injector of claim 19 including a generally cone-shaped threaded flange to cooperate with a corresponding threaded flange on each of the plurality of syringes.

* * * * *

UNITED STATES PATENT AND TRADEMARK OFFICE
CERTIFICATE OF CORRECTION

PATENT NO.         : 7,192,417 B2                                    Page 1 of 1
APPLICATION NO. : 10/233844
DATED              : March 20, 2007
INVENTOR(S)      : Thompson et al.

It is certified that error appears in the above-identified patent and that said Letters Patent is hereby corrected as shown below:

Column 10
_____

Line 20, after "diameter" insert --,--
Line 52, after "at least one" delete "of"

Column 11
_____

Line 19, after "diameter" insert --,--
Line 21, change "chive" to --drive--
Line 54, after "least one" delete "of"

Column 12
_____

Line 29, change "eaAzh" to --each--
Line 39, after "diameter" insert --,--
Line 58, after "radially", delete ","

Column 13
_____

Line 11, please delete first occurrence of "of"

Column 14
_____

Lines 13-14, change "cone-sponding" to --corresponding--

Signed and Sealed this

Eighth Day of April, 2008

JON W. DUDAS
*Director of the United States Patent and Trademark Office*